US012575804B2

(12) United States Patent (10) Patent No.: US 12,575,804 B2
Park et al. (45) Date of Patent: Mar. 17, 2026

(54) BLADDER VOLUME MEASURING DEVICE

(71) Applicant: EDGECARE INC., Seoul (KR)

(72) Inventors: Yul Young Park, Yongin-si (KR);
Hyun Wook Lee, Seoul (KR); **Jung
Jun Kim**, Seoul (KR)

(73) Assignee: Edgecare Inc., Seoul (KR)

( * ) Notice: Subject to any disclaimer, the term of this
patent is extended or adjusted under 35
U.S.C. 154(b) by 79 days.

(21) Appl. No.: 18/436,777

(22) Filed: Feb. 8, 2024

(65) Prior Publication Data

US 2025/0009328 A1 Jan. 9, 2025

(30) Foreign Application Priority Data

Jul. 4, 2023 (KR) ........................ 10-2023-0086176

(51) Int. Cl.
*A61B 8/00* (2006.01)
*A61B 8/08* (2006.01)
(52) U.S. Cl.
CPC .............. *A61B 8/08* (2013.01); *A61B 8/5207*
(2013.01); *A61B 8/5223* (2013.01)
(58) Field of Classification Search
CPC ........ A61B 8/08; A61B 8/5207; A61B 8/5223
See application file for complete search history.

(56) References Cited

U.S. PATENT DOCUMENTS

2017/0124700 A1* 5/2017 Sarojam ................. A61B 8/523

FOREIGN PATENT DOCUMENTS

| JP | 2003190168 A | 7/2003 |
|----|--------------|--------|
| JP | 2009279435 A | 12/2009 |
| JP | 2010527277 A | 8/2010 |
| JP | 2011183142 A | 9/2011 |
| JP | 2012101104 A | 5/2012 |
| JP | 2016539683 A | 12/2016 |
| JP | 2018528041 A | 9/2018 |
| KR | 20070105097 A | 10/2007 |
| KR | 20170066322 A | 6/2017 |
| KR | 20180005812 A | 1/2018 |
| KR | 20200094233 A | 8/2020 |
| KR | 20200128871 A | 11/2020 |

* cited by examiner

*Primary Examiner* — Keith M Raymond
*Assistant Examiner* — Adam D. Kolkin
(74) *Attorney, Agent, or Firm* — ArentFox Schiff LLP;
Yun H. Choe

(57) ABSTRACT

According to the bladder volume measuring device accord-
ing to the present invention, it is possible to more accurately
measure the amount of urine contained in the bladder by
calculating the bladder volume according to the first straight
line and the second straight line crossing the inside of the
bladder region included in the cross-sectional image includ-
ing the bladder.

8 Claims, 9 Drawing Sheets

CROSS-SECTIONAL IMAGE (PI)

BLADDER REGION(BR)

BLADDER(B)

CROSS-SECTIONAL IMAGE (PI)

BLADDER REGION(BR)

| BLADDER SHAPE(BS) |
| --- |
| ELLIPSE |
| RECTANGULAR PARALLELEPIPED |
| TRIANGULAR PRISM |
| SPHERE |

ADDITIONAL
STRAIGHT LINE
SETTING UNIT

AL →

340

LENGTH
MEASURING UNIT

ALL →

BLADDER REGION(BR)

FIG. 9

| BLADDER SHAPE(BS) | WEIGHT(WT) |
|---|---|
| ELLIPSE | 0.81 |
| RECTANGULAR PARALLELEPIPED | 0.89 |
| TRIANGULAR PRISM | 0.66 |
| SPHERE | 0.52 |

BLADDER VOLUME MEASURING DEVICE

CROSS REFERENCE TO RELATED APPLICATION

This application claims priority to the Korean Patent Application No. 10-2023-0086176 filed Jul. 4, 2023, the contents of which are incorporated herein by reference in its entirety.

FIELD OF DISCLOSURE

The present invention relates to a bladder volume measuring device.

BACKGROUND

When urine is sufficiently full in a bladder, a normal person may feel that the bladder is filled with enough urine to urinate, and excrete the urine to the outside. However, the number of patients who have difficulty excreting urine because the patients do not feel it even though the urine is sufficiently full in their bladder has been increasing recently. Various researches are currently being conducted to solve this problem.

SUMMARY

The present invention provides volume measuring device capable of more accurately measuring the amount of urine contained in a bladder by calculating a bladder volume according to a first straight line and a second straight line crossing an inside of a bladder region included in a cross-sectional image including the bladder.

To solve the above problem, a bladder volume measuring device according to an embodiment of the present invention may include an ultrasound transducer, an image generation unit, and a volume calculation unit. The ultrasound transducer may transmit an ultrasound transmission signal to a human bladder and receive an ultrasound reception signal reflected from the bladder. The image generation unit may generate a cross-sectional image including the bladder based on the ultrasound reception signal. The volume calculation unit may calculate the bladder volume according to a first straight line and a second straight line crossing an inside of a bladder region included in the cross-sectional image.

The volume calculation unit may further include a lookup table. The lookup table may determine the bladder volume according to a product of a first straight line length corresponding to a length of the first straight line and a second straight line length corresponding to a length of the second straight line.

The lookup table may include a plurality of sub lookup tables determined according to the product of the first straight line length and the second straight line length. Each of the plurality of sub lookup tables may have a different slope corresponding to a ratio at which the bladder volume linearly increases as the product of the first straight line length and the second straight line length increases.

The bladder volume measuring device may further include a ratio calculation unit. The ratio calculation unit may calculate a length ratio corresponding to the ratio of the first straight line length and the second straight line length.

The bladder volume measuring device may further include a first shape determination unit. The first shape determination unit may determine the bladder shape according to the length ratio.

The bladder volume measuring device may further include an additional straight line setting unit and a length measuring unit. The additional straight line setting unit may set a plurality of additional straight lines crossing the inside of the bladder region while moving at predetermined reference angle intervals in a first direction based on the second straight line. The length measuring unit may measure additional straight line lengths corresponding to lengths of the additional straight lines.

The bladder volume measuring device may further include an additional ratio calculation unit. The additional ratio calculation unit may calculate an additional length ratio corresponding to the ratio of the first straight line length and the additional straight line length.

The bladder volume measuring device may further include a second shape determination unit. The second shape determination unit may determine the bladder shape according to the length ratio and the additional length ratio.

The bladder volume measuring device may further include a weight determination unit. The weight determination unit may determine a weight according to the bladder shape.

The bladder volume may be determined according to the first straight line length, the second straight line length, and the weight.

In addition to the technical problems of the present invention described above, other features and advantages of the present invention will be described below, or may be clearly understood by those skilled in the art from such description and explanation.

BRIEF DESCRIPTION OF DRAWINGS

FIG. 1 is a diagram illustrating a bladder volume measuring device according to embodiments of the present invention.

FIG. 3 is a diagram for describing a lookup table applied to the bladder volume measuring device of FIG. 1.

FIG. 4 is a diagram illustrating a ratio calculation unit and a first shape determination unit included in the bladder volume measuring device of FIG. 1.

FIG. 5 is a diagram for describing an operation of the first shape determination unit included in the bladder volume measuring device of FIG. 1.

FIG. 6 is a diagram illustrating an additional straight line setting unit and a length measuring unit included in the bladder volume measuring device of FIG. 1.

FIG. 9 is a diagram for describing an operation of the weight determination unit included in the bladder volume measuring device of FIG. 1.

DETAILED DESCRIPTION

Figure 2:
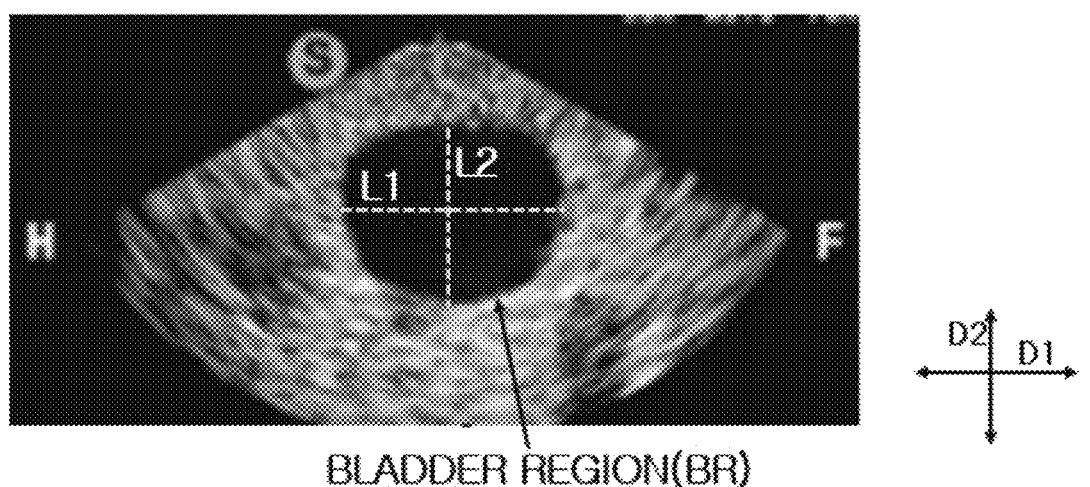
FIG. 2 is a diagram illustrating a cross-sectional image used in the bladder volume measuring device of FIG. 1.

In this specification, in adding reference numerals to components throughout the drawings, it is to be noted that like reference numerals designate like components even though components are illustrated in different drawings.

In this specification, in adding reference numerals to components throughout the drawings, it is to be noted that like reference numerals designate like components even though components are illustrated in different drawings.

On the other hand, the meaning of the terms described in the present specification should be understood as follows.

Singular expressions should be understood as including plural expressions, unless the context clearly defines otherwise, and the scope of rights should not be limited by these terms.

It should be understood that terms such as "include" and "have" do not preclude the existence or addition possibility of one or more other features or numbers, steps, operations, components, parts, or combinations thereof.

Hereinafter, preferred embodiments of the present invention designed to solve the above problems will be described in detail with reference to the accompanying drawings.

Figure 1:
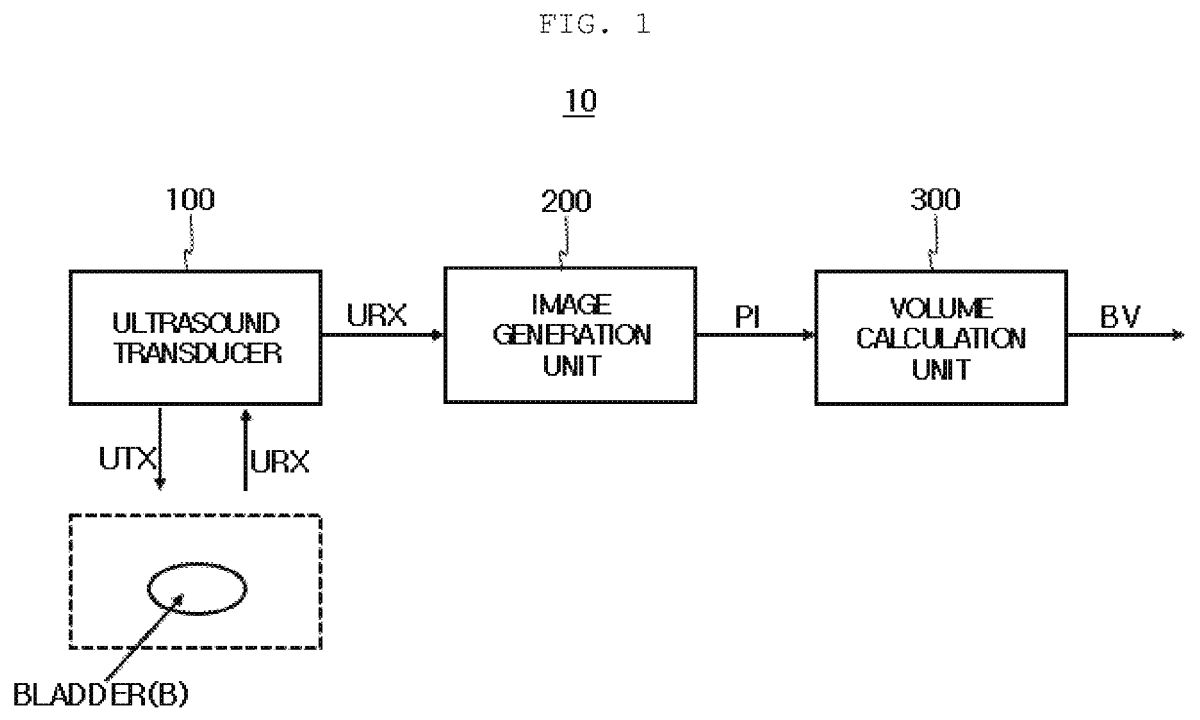
Figure 3:
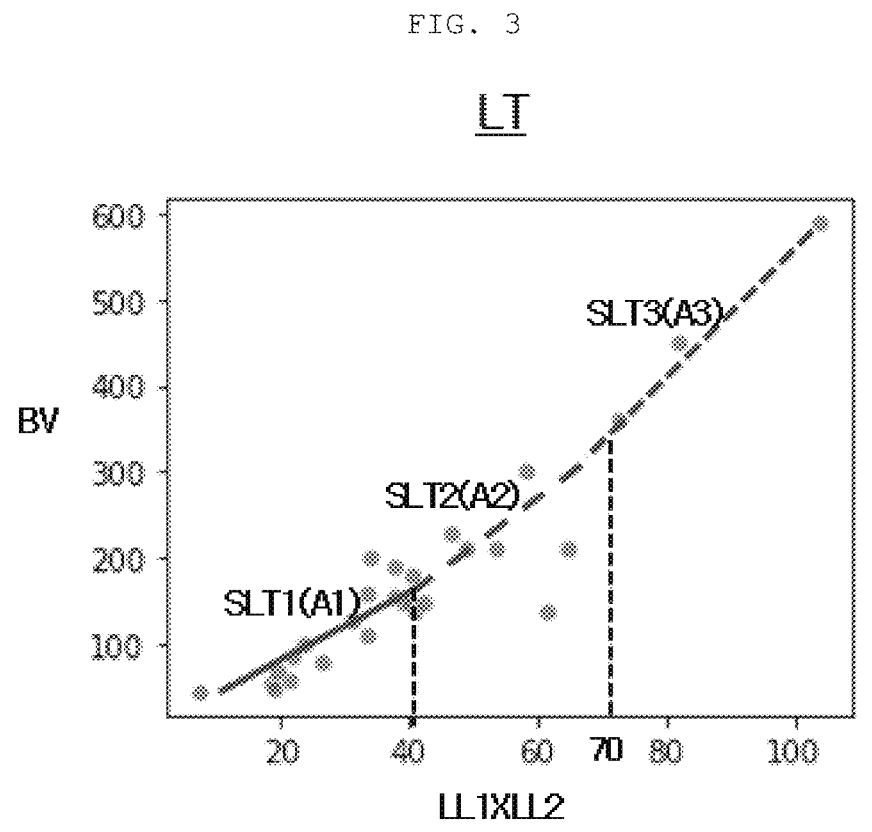

FIG. 1 is a diagram illustrating a bladder volume measuring device according to embodiments of the present invention, FIG. 2 is a diagram illustrating a cross-sectional image used in the bladder volume measuring device of FIG. 1, and FIG. 3 is a diagram for describing a lookup table applied to the bladder volume measuring device of FIG. 1.

Referring to FIGS. 1 to 3, a bladder volume measuring device 10 according to an embodiment of the present invention may include an ultrasound transducer 100, an image generation unit 200, and a volume calculation unit 300. The ultrasound transducer 100 may transmit an ultrasound transmission signal UTX to a human bladder and receive an ultrasound reception signal URX reflected from a bladder B. For example, as illustrated in FIG. 1, the ultrasound transmission signal UTX may be transmitted in a direction of the bladder placed inside the human body using the ultrasound transducer 100, and the ultrasound transducer 100 may receive the ultrasound reception signal URX reflected from around the bladder.

The image generation unit 200 may generate a cross-sectional image PI including the bladder based on the ultrasound reception signal URX. For example, the ultrasound reception signal URX received by the ultrasound transducer 100 may be transmitted to the image generation unit 200, and the image generation unit 200 may process the ultrasound reception signal URX to generate the cross-sectional image PI including an area around the bladder.

The volume calculation unit 300 may calculate a bladder volume BV according to a first straight line L1 and a second straight line L2 crossing an inside of a bladder region BR included in the cross-sectional image PI. For example, the volume calculation unit 300 may extract the bladder region BR from the cross-sectional image PI and set the first straight line L1 and the second straight line L2 crossing the inside of the bladder region BR. The first straight line L1 may be a line connecting points that meet a boundary of the bladder region BR along a first direction D1 based on the bladder region BR, and the second straight line L2 may be a line connecting points that meet the boundary of the bladder region BR along a second direction D2 based on the bladder region BR. Here, the bladder region BR may be a region corresponding to the human bladder B in the cross-sectional image PI.

In one embodiment, the volume calculation unit 300 may further include a lookup table LT. In the lookup table LT, the bladder volume BV may be determined according to a product of a first straight length LL1 corresponding to the length of the first straight line L1 and a second straight length LL2 corresponding to the length of the second straight line L2. For example, the first straight line length LL1 may be 5, and the second straight line length LL2 may be 5. In this case, the product of the first straight line length LL1 and the second straight line length LL2 may be 25. When the product of the first straight length LL1 and the second straight length LL2 is 25, as illustrated in FIG. 3, the bladder volume BV corresponding to the product of the first straight length LL1 and the second straight length LL2 may be 100. Here, the data included in the lookup table LT may be obtained by repeatedly experimentally measuring the bladder volume BV according to the product of the first straight line length LL1 and the second straight line length LL2.

In one embodiment, the lookup table LT may include a plurality of sub lookup tables determined according to the product of the first straight line length LL1 and the second straight line length LL2. Each of the plurality of sub lookup tables may have a different slope corresponding to a ratio at which the bladder volume BV linearly increases as the product of the first straight line length LL1 and the second straight line length LL2 increases. For example, the plurality of sub lookup tables may include a first sub lookup table SLT1, a second sub lookup table SLT2, and a third sub lookup table SLT3. The first sub lookup table SLT1 may be applied when the product of the first straight line length LL1 and the second straight length LL2 is greater than 0 and smaller than 40, and the second sub lookup table SLT2 may be applied when the product of the first straight line length LL1 and the second straight line length LL2 is greater than 40 and smaller than 70. In addition, the third sub lookup table SLT3 may be applied when the product of the first straight line length LL1 and the second straight line length LL2 is greater than 70.

For example, in the first sub lookup table SLT1, the slope corresponding to the ratio at which the bladder volume BV linearly increases as the product of the first straight line length LL1 and the second straight length LL2 increases may be a first slope A1, and in the second sub lookup table SLT2, the slope corresponding to a ratio at which the bladder volume BV linearly increases as the product of the first straight line length LL1 and the second straight length LL2 increases may be a second slope A2. In addition, in the third sub lookup table SLT3, the slope corresponding to the ratio at which the bladder volume BV linearly increases as the product of the first straight length LL1 and the second straight length LL2 increases may be a third slope A3. Here, the third slope A3 may be the greatest and the first slope A1 may be the smallest.

Figure 4:
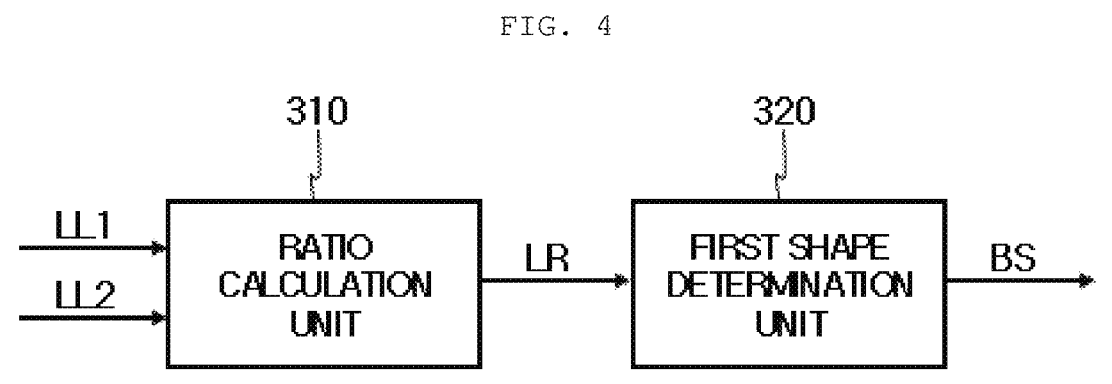

FIG. 4 is a diagram illustrating a ratio calculation unit and a first shape determination unit included in the bladder volume measuring device of FIG. 1 and FIG. 5 is a diagram for describing an operation of the first shape determination unit included in the bladder volume measuring device of FIG. 1.

Referring to FIGS. 1 to 5, in one embodiment, the bladder volume measuring device 10 may further include a ratio calculation unit 310. The ratio calculation unit 310 may calculate a length ratio LR corresponding to the ratio of the first straight length LL1 and the second straight length LL2. For example, the first straight line length LL1 may be 5, and the second straight line length LL2 may be 5. In this case, the ratio calculation unit 310 may calculate 5/5=1, which corresponds to the ratio of the first straight length LL1 and the second straight length LL2, as the length ratio LR.

In one embodiment, the bladder volume measuring device 10 may further include a first shape determination unit 320. The first shape determination unit 320 may determine a bladder shape BS according to the length ratio LR. For example, the bladder shape BS may include an ellipse, a rectangular parallelepiped, a triangular prism, a sphere, and the like. When the length ratio LR is 1, the first shape determination unit 320 may determine the sphere as the bladder shape BS.

According to the bladder volume measuring device 10 according to the present invention, it is possible to more accurately measure the amount of urine contained in the bladder by calculating the bladder volume BV according to the first straight line L1 and the second straight line crossing the inside of the bladder region BR included in the cross-sectional image PI including the bladder.

Figure 6:
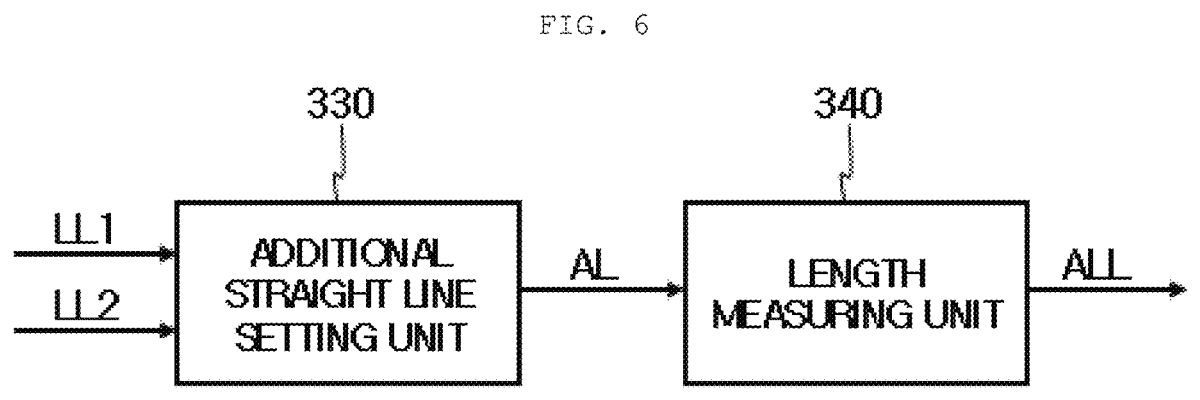
Figure 7:
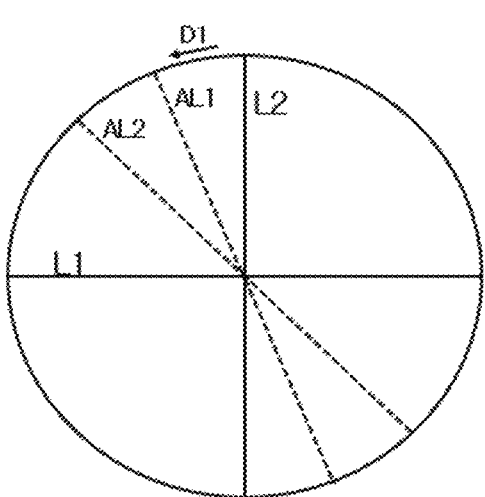
FIG. 7 is a diagram for describing an operation of the additional straight line setting unit included in the bladder volume measuring device of FIG. 1.

FIG. 6 is a diagram illustrating an additional straight line setting unit and a length measuring unit included in the bladder volume measuring device of FIG. 1 and FIG. 7 is a diagram for describing an operation of the additional straight line setting unit included in the bladder volume measuring device of FIG. 1.

Referring to FIGS. 1 to 7, in one embodiment, the bladder volume measuring device 10 may further include an additional straight line setting unit 330 and a length measuring unit 340. The additional straight line setting unit 330 may set a plurality of additional straight lines AL crossing the inside of the bladder region BR while moving at predetermined reference angle intervals in the first direction D1 based on the second straight line L2. As illustrated in FIGS. 4 and 5, when the bladder shape BS is calculated using only the first straight line length LL1 and the second straight line length LL2, it may be difficult to accurately determine the bladder shape BS. Therefore, the additional straight lines AL may be used to more accurately calculate the bladder shape BS. For example, the additional straight line setting unit 330 may set the plurality of additional straight lines AL crossing the inside of the bladder region BR while moving in the first direction D1 based on the second straight line L2. Here, the predetermined reference angle may be 15°. The additional straight line setting unit 330 may set a line connecting points, which meet the boundary of bladder region BR crossing the inside of bladder region BR by moving by 15° in the first direction D1 based on the second straight line L2, as a first additional straight line AL1, and the additional straight line setting unit 330 may set a line connecting points, which meet the boundary of bladder region BR crossing the inside of bladder region BR by moving by 30° in the first direction D1 based on the second straight line L2, as a second additional straight line AL2. In the same way, the additional straight line setting unit 330 may set two or more additional straight lines. Here, the first direction D1 may be clockwise or counterclockwise.

The length measuring unit 340 may measure an additional straight line length ALL corresponding to the lengths of the additional straight lines AL. For example, the plurality of additional straight lines AL may be the first additional straight line AL1 and the second additional straight line AL2. The length measuring unit 340 may measure a first additional straight line length ALL1 corresponding to a length of the first additional straight line AL1 and provide the first additional straight line length ALL1 as 5, and measure a second additional straight line length ALL2 corresponding to a length of the second additional straight line AL2 and provide the second additional straight line length ALL2 as 5.

Figure 8:
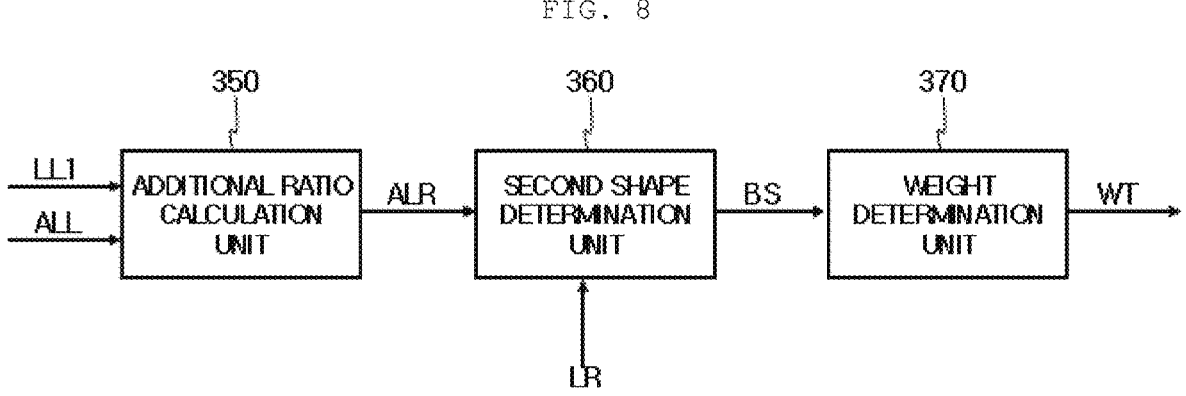
FIG. 8 is a diagram illustrating an additional ratio calculation unit, a second shape determination unit, and a weight determination unit included in the bladder volume measuring device of FIG. 1.

FIG. 8 is a diagram illustrating an additional ratio calculation unit, a second shape determination unit, and a weight determination unit included in the bladder volume measuring device of FIG. 1 and FIG. 9 is a diagram for describing an operation of the weight determination unit included in the bladder volume measuring device of FIG. 1.

Referring to FIGS. 1 to 9, in one embodiment, the bladder volume measuring device 10 may further include an additional ratio calculation unit 350. The additional ratio calculation unit 350 may calculate an additional length ratio ALR corresponding to a ratio of the first straight line length LL1 and the additional straight line length. For example, the plurality of additional straight lines AL may be the first additional straight line AL1 and the second additional straight line AL2. The first additional straight line length ALL1 may be 5, and the second additional straight line length ALL2 may be 5. In this case, the additional ratio calculation unit 350 may provide 5/5=1 as a first additional length ratio ALR1 corresponding to a ratio of the first straight line length LL1 and the first additional straight length ALL1, and the additional ratio calculation unit 350 may provide 5/5=1 as a second additional length ratio ALR2 corresponding to a ratio of the second straight line length LL2 and the second additional straight line length ALL2.

In one embodiment, the bladder volume measuring device 10 may further include a second shape determination unit 360. The second shape determination unit 360 may determine the bladder shape BS according to the length ratio LR and the additional length ratio ALR. For example, when the length ratio LR is 1, the first additional length ratio ALR1 is 1, and the second additional length ratio ALR2 is 1, the second shape determination unit may determine the bladder shape BS to be a sphere.

As one embodiment, the bladder volume measuring device 10 may further include a weight determination unit 370. The weight determination unit 370 may determine a weight WT according to the bladder shape BS. For example, the weight WT applied to calculate the bladder volume BV may be different according to the bladder shape BS. When the bladder shape BS is an ellipse, the weight WT may be 0.81, and when the bladder shape BS is a rectangular parallelepiped, the weight WT may be 0.89. In addition, when the bladder shape BS is a triangular prism, the weight WT may be 0.66, and when the bladder shape BS is a sphere, the weight WT may be 0.52.

In one embodiment, the bladder volume BV may be determined according to the first straight line length LL1, the second straight line length LL2, and the weight WT. For example, the final bladder volume BV may be determined by multiplying the bladder volume BV, which is the product of the first straight length LL1 and the second straight length LL2, by the weight WT.

According to the bladder volume measuring device 10 according to the present invention, it is possible to calculate the shape coefficient based on the information about the bladder shape BS generated from the determination unit that performs the artificial intelligence learning on the bladder ultrasound image big data and more accurately measure the amount of urine contained in the bladder by calculating the bladder volume BV based on the ultrasound image and the shape coefficient.

According to the present invention as described above, the following effects are obtained.

According to the bladder volume measuring device according to the present invention, it is possible to more accurately measure the amount of urine contained in the bladder by calculating the bladder volume according to the first straight line and the second straight line crossing the inside of the bladder region included in the cross-sectional image including the bladder.

In addition, other features and advantages of the present invention may be newly understood through the embodiments of the present invention.

In addition to the technical problems of the present invention described above, other features and advantages of the present invention will be described below, or may be clearly understood by those skilled in the art from such description and explanation.

The invention claimed is:

1. A bladder volume measuring device, comprising:

an ultrasound transducer that transmits an ultrasound transmission signal to a human bladder and receives an ultrasound reception signal reflected from the bladder;

a processor configured to generate a cross-sectional image including the bladder based on the ultrasound reception signal; and a processor configured to calculate a bladder volume according to a first straight line and a second straight line crossing an inside of a bladder region included in the cross-sectional image, wherein the processor configured to calculate the bladder volume includes a lookup table that determines the bladder volume according to a product of a first straight line length corresponding to a length of the first straight line and a second straight line length corresponding to a length of the second straight line; and wherein the lookup table includes a plurality of sub lookup tables determined according to the product of the first straight line length and the second straight line length, and each of the plurality of sub lookup tables has a different slope corresponding to a ratio at which the bladder volume linearly increases as the product of the first straight line length and the second straight line length increases.

2. The bladder volume measuring device of claim 1, further comprising:

a processor configured to calculate a length ratio corresponding to a ratio of the first straight line length and the second straight line length.

3. The bladder volume measuring device of claim 2, further comprising:

a processor configured to determine a first shape that determines a bladder shape according to the length ratio.

4. The bladder volume measuring device of claim 3, further comprising:

an additional processor configured to set a plurality of additional straight lines crossing the inside of the bladder region while moving at predetermined reference angle intervals in a first direction based on the second straight line; and a processor configured to measure additional straight line lengths corresponding to lengths of the additional straight lines.

5. The bladder volume measuring device of claim 4, further comprising:

an additional processor configured to calculate an additional length ratio corresponding to the ratio of the first straight line length and the additional straight line length.

6. The bladder volume measuring device of claim 5, further comprising:

a second processor configured to determine the second bladder shape according to the length ratio and the additional length ratio.

7. The bladder volume measuring device of claim 6, further comprising:

a processor configured to determine a weight according to the second bladder shape.

8. The bladder volume measuring device of claim 7, wherein the bladder volume is determined according to the first straight line length, the second straight line length, and the weight.

* * * * *